United States Patent [19]
Kedem

[11] Patent Number: 5,197,984
[45] Date of Patent: Mar. 30, 1993

[54] SHUT-OFF DEVICE PARTICULARLY AS AN ARTIFICIAL SPHINCTER

[75] Inventor: Dan Kedem, Rehovot, Israel

[73] Assignee: Du-Kedem Technologies (Ltd.), Rehovot, Israel

[21] Appl. No.: 721,078

[22] Filed: Jun. 26, 1991

[51] Int. Cl.$^5$ ................................................ A61F 2/08
[52] U.S. Cl. ...................................... 623/14; 604/351; 128/DIG. 25
[58] Field of Search .............................. 604/332-335; 623/12, 14; 128/DIG. 25; 251/4

[56] References Cited

U.S. PATENT DOCUMENTS

| | | | |
|---|---|---|---|
| 3,188,070 | 6/1965 | Lee | 251/4 |
| 4,401,107 | 8/1983 | Haber et al. | 623/14 |
| 4,705,518 | 11/1987 | Baker et al. | 600/31 |

Primary Examiner—Randall L. Green
Assistant Examiner—R. Clarke
Attorney, Agent, or Firm—Benjamin J. Barish

[57] ABSTRACT

A shut-off device particularly useful as an artifical sphincter for shutting-off the flow from a passage in a subject's body includes a conduit assembly attachable to the body with its inner end in alignment with the passage, a ring rotatably mounted in the outer end of the conduit assembly, and an elastomeric sleeve passing through the conduit assembly and ring, with the inner end of the sleeve attached to the inner end of the conduit assembly, and the outer end of the sleeve attached to the ring. The pliable sleeve is of a length such that the ring may be rotated with respect to the conduit assembly to twist the pliable sleeve from an untwisted open condition permitting the flow of the material from the body passage, to a twisted closed condition shutting-off the flow of the material.

18 Claims, 2 Drawing Sheets

SHUT-OFF DEVICE PARTICULARLY AS AN ARTIFICIAL SPHINCTER

FIELD AND BACKGROUND OF THE INVENTION

The present invention relates to shut-off devices for shutting-off the flow of a material from a passage in a body. The invention is particularly useful as an artificial sphincter for shutting-off a channel in a patient's body communicating with an opening through the skin of the patient's body. The invention is therefore described below with respect to such application, but it will be appreciated that the invention could advantageously be used in other applications as well.

Various types of ostomy/ileostomy procedures are used to correct difficulties in the intestinal track, such as an obstruction or cancer. In such a surgical procedure, the intestine is usually severed, and an end of the intestine is brought through an incision in the abdominal wall and is secured adjacent the patient's skin, forming an opening, or "stoma", to permit passage of stool material. Such a procedure results in loss of fecial continence for the patient, and therefore the patient is usually required to wear a stool pouch on the outside of the body in order to collect the stool passing through the stoma. Various types of artificial sphincters have been devised, including mechanical and magnetic types, in order to eliminate the need for wearing external stool pouches. However, the known artificial sphincters have not proved satisfactory, and therefore in most cases the patient must still wear stool pouches despite the aesthetic, social and emotional problems involved.

OBJECTS AND BRIEF SUMMARY OF THE INVENTION

A broad object of the present invention is to provide a novel shut-off device for shutting-off flow of a material from a passage in a body.

Another more particular object of the invention is to provide an artificial sphincter for shutting-off a channel, such as an intestine, in a subject's body, which artificial sphincter has a number of important advantages over the previously known devices as will be described below.

According to one aspect of the present invention, there is provided a shut-off device for shutting-off the flow of a material from a passage in a body, comprising: a conduit assembly attachable to the body with its inner end in alignment with the passage; a ring rotatably mounted in the outer end of the conduit assembly; and a pliable sleeve passing through the conduit assembly and the ring, with the inner end of the sleeve attached to the inner end of the conduit assembly, and the outer end of the sleeve attached to the ring; the pliable sleeve being of a length such that the ring may be rotated with respect to the conduit assembly to twist the pliable sleeve from an untwisted open condition permitting the flow of the material therethrough form the passage in the body, to a twisted closed condition shutting-off the flow of the material therethrough.

According to another aspect of the present invention, there is provided a shut-off device as described above but particularly for use as an artificial sphincter for shutting-off a channel in a subject's body communicating with an opening through the skin of the subject's body, comprising: a conduit assembly attachable to the subject's body with its inner end attached to and in alignment with the channel and with its outer end attached to the subject's skin and in alignment with an opening therethrough; a ring rotatably mounted in the outer end of the conduit assembly; and a pliable sleeve passing through the conduit assembly and the ring, with the inner end of the sleeve attached to the inner end of the conduit assembly, and the outer end of the sleeve attached to the ring; the pliable sleeve being of a length such that the ring may be rotated with respect to the conduit assembly to twist the pliable sleeve from an untwisted open condition permitting the flow of the material therethrough from the channel in the subject's body, to a twisted closed condition shutting-off the flow of the material therethrough.

According to further features in the described preferred embodiment, the pliable sleeve is made of an elastomeric material. In addition, the ring is rotatably mounted to the conduit assembly by teeth movable in helical grooves arranged to axially displace the ring outwardly of the outer end of the conduit assembly when the ring is rotated to the open untwisted condition of the pliable sleeve Further, the conduit assembly includes an inner section and an outer section axially adjustable with respect to the inner section An artificial sphincter constructed in accordance with the foregoing features may be conveniently operated by the patient to open or close the sphincter whenever desired, thereby eliminating the need for an external stool pouch. When the sphincter is closed, it effectively seals the channel and need not protrude from the patient's skin. When the sphincter is opened, the rotatable ring moves slightly outwardly of the patient's skin to facilitate removing the fecial matter. Such a spincter provides a number of other important advantages as will be described more particularly below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
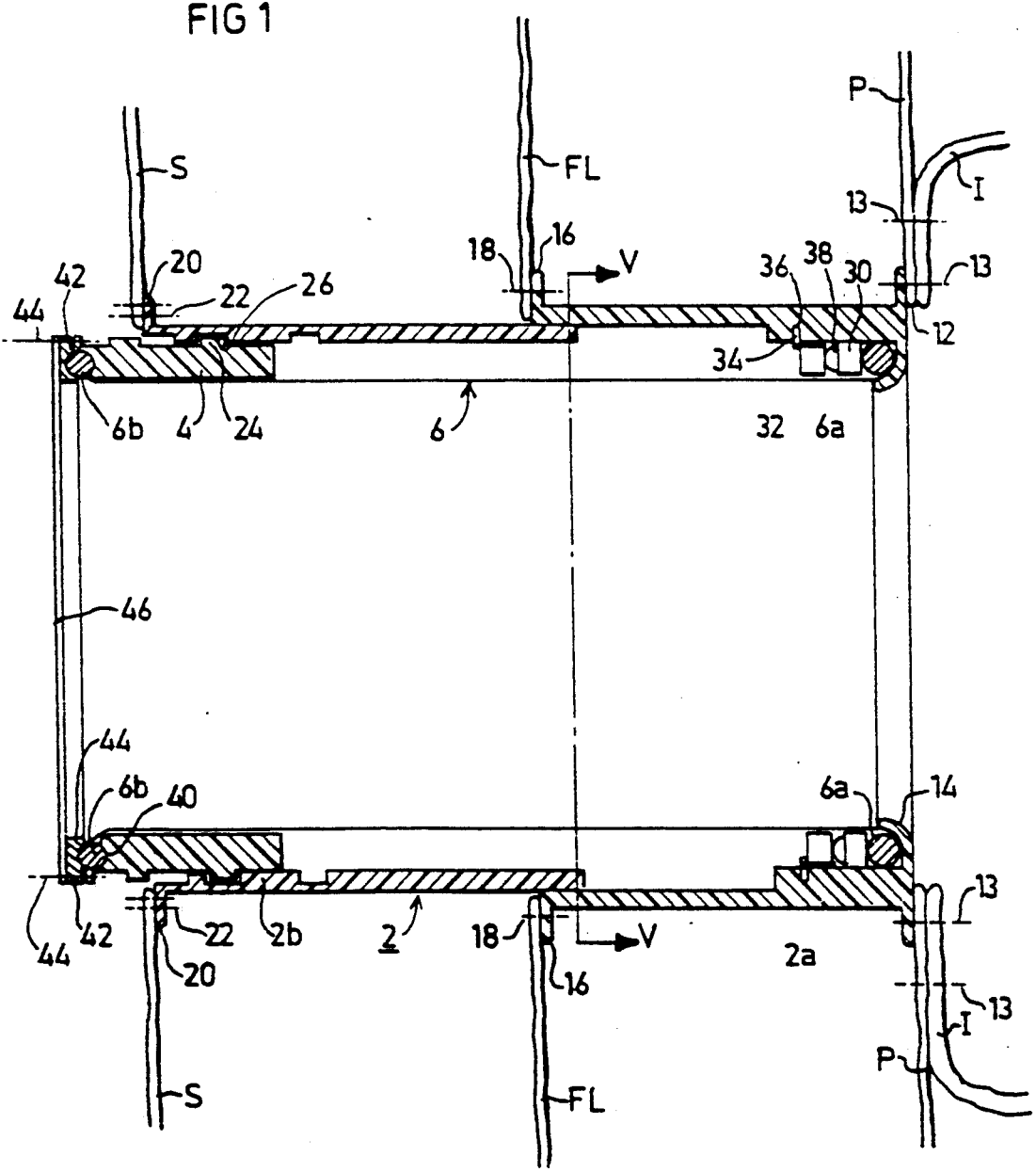
FIG. 1 is a longitudinal sectional view illustrating one form of artificial sphincter constructed in accordance with the present invention, FIG. 1 illustrating the sphincter in its open condition.

The shut-off device illustrated in the drawings is an artificial sphincter for the closure of a stoma formed in a patient's body who has undergone a colostomy/ileostomy. It includes three main units, namely: a conduit assembly 2 attachable at its inner end to the peritoneum P of the patient's body aligned with the open end of the intestine I, and at its outer end to the skin S of the patient's body aligned with an opening therein; a rotatable ring 4 rotatably mounted in the outer end of the conduit assembly 2; and a pliable sleeve or liner 6 passing through the interior of the conduit assembly 2 and ring 4, with the opposite ends 6a, 6b of the sleeve attached thereto.

Figure 2:
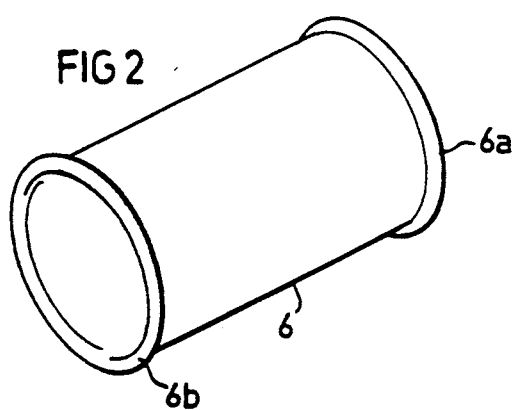
FIGS. 2 and 3 illustrate the pliable sleeve in the sphincter of FIG. 1 in its open and closed conditions, respectively.
Figure 3:
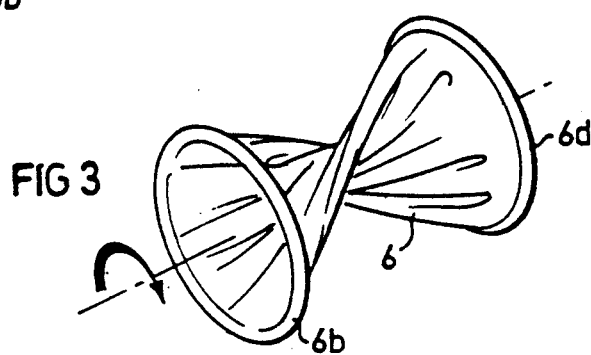

The pliable sleeve 6 is preferable in the form of an elastomeric bladder. It is of a length such that ring 4 may be rotated with respect to conduit assembly 2 to rotate the sleeve 6 from an untwisted open condition as shown in FIG. 2 permitting the flow of material therethrough, to a twisted closed condition as shown in FIG. 3 shutting off the flow of material therethrough.

Figure 4:
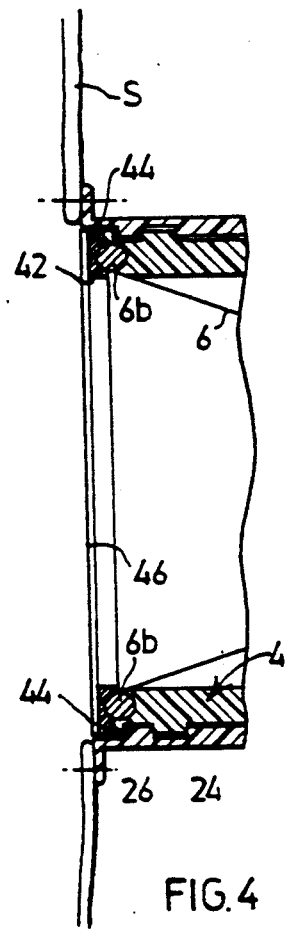
FIG. 4 is a fragmentary view illustrating the outer end of the sphincter of FIG. 1 with the pliable sleeve in its closed condition (the condition illustrated in FIG. 3)

FIG. 1 illustrates the artificial sphincter in the open (FIG. 2) condition of its pliable sleeve 6, whereas FIG. 4 is a fragmentary view illustrating the outer part of the artificial sphincter in the closed condition (FIG. 3) of its sleeve 6.

The conduit assembly 2 includes an inner section 2a and an outer telescoping section 2b both of tubular configuration. The inner section 2a is formed with an external annular flange 12 for attachment by stitches 13 to the peritoneum P and to the open end of the intestine I. This end of section 2a is further formed with an inner annular flange 14 of curved configuration for receiving the respective end 6a of the pliable sleeve 6 which is formed with a thickened bead for this purpose.

The inner section 2a of the conduit assembly 2 is also formed with an annular flange 16 for attachment, by stitches 18, to the fascia layer FL of the patient's body. This layer separates the inner tissue from the outer layer of fat.

The outer end of the outer conduit section 2b is formed with an annular flange 20 for attachment by stitches 22 to the patient's skin S. Ring 4, which receives the outer end 6b of the pliable sleeve 6, is movable both rotatably and axially with respect to section 2b of the conduit assembly. For this purpose, ring 4 is formed on its outer face with two pairs of teeth 24 received within two pairs of helical grooves 26 formed on the inner face of conduit section 2b.

The thickened bead 6a at the inner end of the pliable sleeve 6 is fixed to flange 14 of the inner conduit section 2a by a clamping ring 30 and a locking ring 32 slidably received within the inner end of conduit section 2a. Locking ring 32 is provided with a plurality (e.g., four) of pivotal fingers 34 equally spaced around its circumference and receivable within an annular groove 36 formed on the inner face of conduit section 2a. An annular spring 38 of arcuate cross-section is interposed between locking ring 32 and clamping ring 30, and presses the latter ring firmly against the thickened bead 6b of the pliable sleeve 6, to thereby firmly clamp it against the inner flange 14 of conduit section 2.

The outer end of the rotatable ring 4 is formed with an annular semi-spherical recess 40 for receiving the thickened bead 6b at the outer end of the pliable sleeve 6. A clamping ring 42, also formed with a semi-spherical recess, is fixed by fasteners 44 to the outer end of ring 4 for securely clamping to it that end of the pliable sleeve. The outer end of clamping ring 42 is covered by a removable cap 46, as shown in FIG. 4.

When ring 4 is rotated with respect to section 2b of the conduit assembly 2, the two pairs of teeth 24 in ring 4, moving in the helical grooves 26 of conduit 26, cause the outer end 6b of the pliable sleeve 6 to move both rotationally and axially with respect to the conduit section 2b.

The two parallel helical grooves 26 are so arranged that when end 6b of the pliable sleeve 6 is in its twisted, closed condition as illustrated in FIG. 3, the outer end of the clamping ring 42 is substantially flush with the subject's skin, as shown in FIG. 4; whereas when the pliable sleeve is moved to its untwisted open condition, as illustrated in FIG. 2, the clamping ring 42 projects outwardly of the patient's skin as shown in FIG. 1. This arrangement facilitates the attachment of a receptacle or other device for receiving the material to be discharged when the pliant sleeve 6 is opened, whereas when it is closed it does not produce any unsightly or disturbing projection from the skin.

The outer conduit section 2b is coupled to the inner conduit section 2a by a coupling arrangement which permits section 2b to be conveniently adjusted axially with respect to conduit section 2a. This adjusting arrangement is more particularly illustrated in FIGS. 5 and 6.

Figure 5:
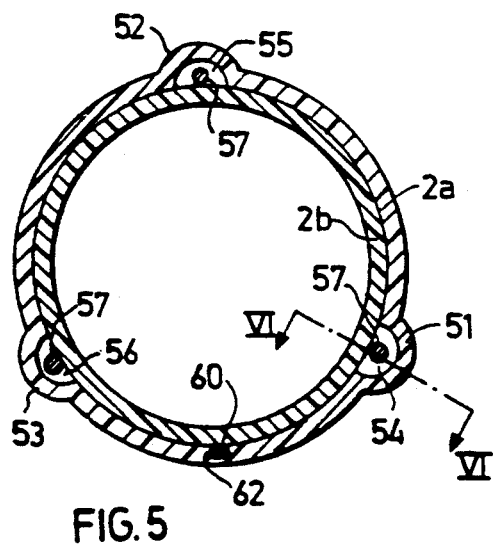
FIG. 5 is a transverse sectional view along line V—V of FIG. 1.
Figure 6:
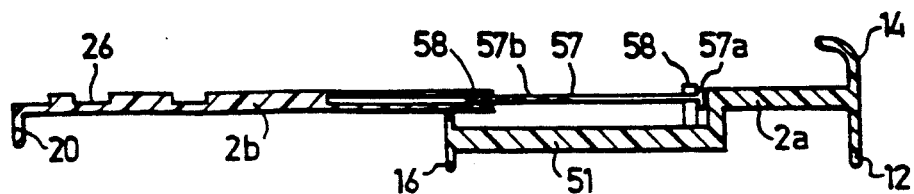
FIG. 6 is a sectional view along line VI—VI of FIG. 5.

Thus, as shown in FIG. 5, conduit section 2a is formed with three axially-extending bulges 51, 52, 53, equally spaced about the circumference of the conduit section, to define three axially-extending channels 54–56. Each channel receives an elongated rod 57. As shown particularly in FIG. 6, each of the elongated rods 57 passes through an opening formed in a ledge 58 fixed to conduit section 2a. One end of each rod 57 is formed with an enlarged head 57a engageable with one face of its respective ledge 58, and the opposite end 57b of the rod is threaded and is received within a threaded bore 58 formed in the respective end of conduit section 2b.

Such an arrangement permits the effective length of the conduit assembly to be changed whenever required, e.g., as the patient loses or gains weight as a result of changes in the thickness of the fat layer between the fascia layer FA (FIG. 1) and the outer skin S of the patient. When conduit section 2b is thus adjusted with respect to conduit section 2a, a rib 60 (FIG. 5) in the outer face of section 2b is moved within an axial recess 62, formed in the inner face of section 2a, and thereby prevents any rotary displacement of one section with respect to the other.

The manner of applying and using the illustrated artificial sphincter will now be described:

In a surgical procedure, conduit assembly 2 is fixed in place in the patient's body by applying: stitches 13 to the annular flange 12 of the inner section 2a, the peritoneum P and the open end of the intestine I; stitches 18 to flange 16 of the inner section 2a and the patient's fascia F; and stitches 22 to the annular flange 20 of the outer section 2b and the patient's skin S. Before this is done, the effective length of the outer conduit section 2b is first pre-adjusted, particularly according to the thickness of the fat layer between the fascia layer FL and skin S of the patient, by adjusting the threaded rods 57 carried by section 2a within the bores 58 carried by section 2b, as shown particularly in FIG. 6.

The thickened bead 6a at the inner end of the pliable sleeve 6 is then clamped to conduit section 2a by applying clamping ring 30 and locking ring 32, with the annular leaf spring 38 interposed between the two rings. Ring 32 is locked to the inner face of section 2a by pivoting fingers 34 into the annular recess 36 in the inner face of that section. Spring 38 thus presses clamping ring 30 firmly against the thickened bead 6a, thereby firmly clamping that end of the pliable sleeve 6 to the inner flange 14 in section 2a.

The rotatable ring 4 may then be received within the outer end of section 2b of the fixed conduit assembly 2 by threading the teeth 24 of ring 4 into the grooves 26 of section 2b. For this purpose, the teeth 24 and grooves 26 may have two starting points, similar to the Luerlock in syringes. The thickned bead 6b of the pliable sleeve 6 is then applied to ring 4 and is fixed thereto by clamping ring 42 and fasteners 44.

As mentioned earlier, the teeth 24 and grooves 26, in the rotatable ring 4 and the fixed conduit section 2b, are such that when ring 4 is rotated to bring the pliable sleeve to its untwisted, open condition, as illustrated in FIG. 2, the outer end of the ring projects outwardly of the skin, and thereby provides a convenient attachment for a receptacle or the like for receiving the material to be discharged through the artificial sphincter. In this open, untwisted condition of the pliable sleeve 6, the sleeve is preferably under tension so as to firmly hold the sleeve in its open condition.

On the other hand, when the artificial sphincter is to be closed, ring 4 is rotated, e.g., about one-full rotation, sufficiently to twist the pliable sleeve 6 to its closed, twisted condition, as illustrated in FIG. 3. This rotation of ring 4 also moves it inwardly of the fixed conduit section 2b so that the outer surface of the ring becomes substantially flush with the patient' skin S. This avoids the creation of an unsightly and disturbing bulge or projection from the patient's skin. When the pliable sleeve 6 has been twisted to its closed condition as illustrated in FIG. 3, the artificial sphincter is closed by cap 46 applied over the outer end of ring 4.

The illustrated spincter thus enables complete voluntary control of bowel evacuation by a simple manual procedure and allows the disposal of the stool, whether liquid or solid, without exposing it to external air. It thereby eliminates the need for a stool bag. Moreover, when the spincter is closed, it does not protrude from the body. It also allows the adminstration of an enema. The illustrated sphincter thus enables the patient to carry out most activities in a substantial normal way with the abdominal wall closed and with no bag attached to it.

The illustrated artificial sphincter can be applied with a minimal prolongation in the duration of the initial surgery, and the pliable sleeve 6 may be later replaced by a technician without the need for surgery. The illustrated sphincter also permits its length to be changed without surgery, e.g., as may be required when the subject loses or gains weight.

While the invention has been described with respect to an artificial sphincter, it will be appreciated that the invention could also be used in other types of shut-off devices, for example manually-operated valves. Many other variations, modifications and applications of the invention will be apparent.

What is claimed is:

1. A shut-off device for shutting-off the flow of a material form a passage in a body, comprising:
    a conduit assembly attachable to said body with its inner end in alignment with said passage;
    a ring rotatably mounted in the outer end of said conduit assembly;
    and a pliable sleeve passing through said conduit assembly and said ring, with the inner end of the sleeve attached to the inner end of said conduit assembly, and the outer end of the sleeve attached to said ring;
    said pliable sleeve being of a length such that said ring may be rotated with respect to said conduit assembly to twist the pliable sleeve from an untwisted open condition permitting the flow of the material therethrough from said passage in the body, to a twisted closed condition shutting-off the flow of the material therethrough;
    said ring being rotatably mounted with respect to said conduit assembly so as to move axially away from the outer end of the conduit assembly when the ring is rotated to the open untwisted condition of the pliable sleeve, to thereby increase the tension therein when in said open untwisted condition.

2. The device according to claim 1, wherein said pliable sleeve is made of an elastomeric material.

3. The device according to claim 1, wherein said ring is rotatably mounted to said conduit assembly by teeth received within helical grooves arranged to axially displace said ring outwardly of the outer end of said conduit assembly when said ring is rotated to said open untwisted condition of the pliable sleeve.

4. The device according to claim 1, wherein said opposite ends of the pliable sleeve are formed with thickened beads for attaching them to said conduit assembly and rotatable ring.

5. The device according to claim 4, wherein the thickened bead of the pliable sleeve is attached to the inner end of said conduit assembly by means of a clamping ring clamping the thickened bead between it and an annular flange formed in the inner end of the conduit assembly.

6. The device according to claim 5, wherein said clamping ring is coupled to said conduit assembly by a locking ring removably attached to said conduit assembly.

7. The device according to claim 6, wherein said locking ring is removably attached to said conduit assembly by a plurality of fingers pivotally mounted to said locking ring to seat within an annular groove formed in the inner face of the inner end of the conduit assembly.

8. The device according to claim 6, wherein an annular spring is interposed between said clamping and locking rings and urges said clamping ring towards said thickened bead to firmly clamp it between the clamping ring and said annular flange of said conduit assembly.

9. The device according to claim 1, wherein said device is an artificial sphincter and includes means for attaching the inner end of the conduit assembly to a subject's body in alignment with a channel therein, and the outer end of the conduit assembly to the outer skin of the subject's body in alignment with an opening therethrough.

10. A shut-off device for shutting-off the flow of a material from a passage in a body, comprising:
    a conduit assembly attachable to said body with its inner end in alignment with said passage;
    a ring rotatably mounted in the outer end of said conduit assembly;
    and a pliable sleeve passing through said conduit assembly and said ring, with the inner end of the sleeve attached to the inner end of said conduit assembly, and the outer end of the sleeve attached to said ring;
    said pliable sleeve being of a length such that said ring may be rotated with respect to said conduit assembly to twist the pliable sleeve from an untwisted open condition permitting the flow of the material therethrough from said passage in the body, to a twisted closed condition shutting-off the flow of the material therethrough;

said conduit assembly including an inner section and an outer section axially adjustable with respect to said inner section.

11. The device according to claim 10, wherein said two sections are axially adjustable by a plurality of rods having enlarged heads engageable with one of said sections and threaded ends receivable in threaded openings formed in the other of said sections.

12. An artificial sphincter for shutting-off the flow of a material from a channel in a subject's body, comprising:

a conduit assembly having an inner end and an outer end;

means for attaching said inner end of the conduit assembly to the subject's body in alignment with said channel;

means for attaching said outer end of said conduit assembly to the subject's skin in alignment with an opening therethrough;

a ring rotatably mounted in the outer end of said conduit assembly;

and a pliable sleeve passing through said conduit assembly and said ring, with the inner end of the sleeve attached to the inner end of said conduit assembly, and the outer end of the sleeve attached to said ring;

said pliable sleeve being of a length such that said ring may be rotated with respect to said conduit assembly to twist the pliable sleeve from an untwisted open condition permitting the flow of the material therethrough from said channel in the subject's body, to a twisted closed condition shutting-off the flow of the material therethrough;

said conduit assembly including an inner section and an outer section axially adjustable with respect to said inner section.

13. The sphincter according to claim 12, wherein said pliable sleeve is made of an elastomeric material.

14. The sphincter according to claim 12, wherein said ring is rotatably mounted to said conduit assembly by two pairs of teeth received within helical grooves arranged to axially displace said ring outwardly of the outer end of said conduit assembly when said ring is rotated to said open untwisted condition of the pliable sleeve.

15. The sphincter according to claim 13, wherein said two sections are axially adjustable by a plurality of rods having enlarged heads engageable with one of said sections and threaded ends receivable in threaded openings formed in the other of said sections.

16. The sphincter according to claim 12, wherein said opposite ends of the pliable sleeve are formed with thickened beads for attaching them to the inner end of said conduit assembly and to said rotatable ring.

17. The sphincter according to claim 16, wherein the thickened bead of the pliable sleeve is attached to the inner end of said conduit assembly by means of a clamping ring clamping the thickened bead between it and an annular flange formed in the inner end of the conduit assembly, a locking ring removably attached to the conduit assembly, and an annular spring interposed between said clamping and locking rings and urging said clamping ring towards said thickened bead to firmly clamp it between the clamping ring and said annular flange of the conduit assembly.

18. The sphincter according to claim 17, wherein said locking ring is removably attached to said conduit assembly by a plurality of fingers pivotally mounted to said locking ring to seat within an annular groove formed in the inner face of the inner end of the conduit assembly.

* * * * *